United States Patent [19]

Poirier et al.

[11] 4,295,939

[45] Oct. 20, 1981

[54] METHOD AND DEVICE FOR DETECTING A GASEOUS ANHYDRIDE IN AN OXYGEN BEARING GAS

[75] Inventors: Marc Poirier, Chomedey; Michel Gauthier, Laprairie; André Belanger, Ste-Julie, all of Canada

[73] Assignee: Hydro-Quebec, Montreal, Canada

[21] Appl. No.: 98,978

[22] Filed: Nov. 30, 1979

[30] Foreign Application Priority Data

Mar. 30, 1979 [CA] Canada ............................. 324693

[51] Int. Cl.$^3$ ........................................... G01N 27/58
[52] U.S. Cl. ............................ 204/1 T; 204/195 S
[58] Field of Search ................. 204/1 S, 195 S, 1 F, 204/1 K

[56] References Cited

U.S. PATENT DOCUMENTS

| | | | |
|---|---|---|---|
| 362,248 | 11/1871 | Chand | 204/195 |
| 3,403,090 | 9/1968 | Tajiri et al. | 204/1 S |
| 3,776,831 | 12/1973 | Rot et al. | 204/195 S |
| 3,803,006 | 4/1974 | Krueger | 204/1 T |
| 3,914,169 | 10/1975 | Horowitz | 204/195 S |
| 4,187,161 | 2/1980 | Fischer | 204/195 S |

FOREIGN PATENT DOCUMENTS

| | | |
|---|---|---|
| 2454659 | 5/1976 | Fed. Rep. of Germany . |
| 2556483 | 3/1977 | Fed. Rep. of Germany ... 204/195 S |
| 2272395 | 12/1975 | France .................. 204/195 S |

*Primary Examiner*—G. L. Kaplan

*Attorney, Agent, or Firm*—Robic, Robic & Associates

[57] ABSTRACT

A method and a device for detecting a gaseous anhydride and measuring its concentration in an oxygen-bearing gas. The method comprises the following steps: (a) forming an electrolytic junction by contact between a first solid-electrolyte element containing oxyanions of the anhydride to be detected and a second, $O^{--}$ ion-conducting solid-electrolyte element such as stabilized zirconia; (b) bringing this electrolytic junction into contact with the gas containing the gaseous anhydride to be detected so as to form a triple junction; (c) creating at this triple junction a difference of potential measurable by means of two reference electrodes in contact with the first and second electrolyte elements respectively, by fixation of a constant potential in the vicinity of each of these reference electrodes, which themselves are spatially removed from the triple junction; (d) heating the triple junction to such a temperature that a logarithmic variation in the concentration of the anhydride to be detected produces a proportional, substantially linear variation in the difference of potential at the triple junction, this temperature being lower than the melting temperatures of the first and second electrolyte elements; and (e) measuring this difference of potential by means of a potentiometer connected to the reference electrodes so as to obtain a measurement of the concentration of the anhydride to be detected. This method and device may advantageously be used for detecting sulfur carbon anhydrides.

31 Claims, 7 Drawing Figures

METHOD AND DEVICE FOR DETECTING A GASEOUS ANHYDRIDE IN AN OXYGEN BEARING GAS

The present invention relates to a method and a device for detecting a gaseous anhydride and measuring its concentration in an oxygen-bearing gas.

More specifically, this invention relates to a method and to an electrochemical device for detecting a gaseous anhydride and measuring its concentration in an oxygen-bearing gas, by measuring a difference of potential using an electrolytic junction formed by two solid-state electrolyte elements.

Several electrochemical methods are already known for the detection of gaseous anhydrides, which methods are based on the measurement of a potential difference using a solid-state electrolyte element. Such methods are for example described in Canadian Pat. Nos. 1.002.599 and 1.040.264 issued on Dec. 28, 1976 and Oct. 10, 1978 respectively, both in the name of the Applicant. These methods all consist in measuring the activity of the gaseous anhydride to be detected by measuring the difference of potential existing between the two faces of a solid-electrolyte element containing oxyanions of the anhydride to be detected. The difference of potential is measured using a reference electrode and a detection electrode located at a distance from each other but both in direct contact with the surface of the solid-electrolyte element. To create this difference of potential, the surface of the solid-electrolyte element close to the reference electrode is brought into contact with a gaseous anhydride identical to the one to be detected at a known constant concentration and the surface of the same element close to the detection electrode is placed in contact with the gas containing the anhydride to be detected.

According to each of the known methods, the activity of the anhydride to be detected is measured at the metal reference electrode or at the metal detection electrode, where a triple contact is established between the solid-electrolyte element, the gaseous phase containing an anhydride concentration that is either known or to be detected, and the metal electrode itself.

This triple contact between a solid-electrolyte element, a gaseous phase and a metal electrode is also found in the various known methods for detecting oxygen and measuring its concentration in a gas, such as described in U.S. Pat. No. 3,400,054 issued to R. J. Ruka et al. on Sept. 3, 1968.

Although the devices used in practice to set into operation the various known methods mentioned above have so far proved relatively efficient, they are all nevertheless subject to aging. The reason for this is that the gas containing the gaseous anhydride to be detected, which may be heavily contaminated, is permanently in contact with the metal, such as platinum, which composes the electrodes. Furthermore, this permanent contact can sometimes give rise to undesired catalytic reactions.

An object of the present invention is to provide an electrochemical method for detecting a gaseous anhydride and measuring its concentration in an oxygen-containing gas, based on measurement of a difference of potential using a solid-electrolyte junction, which method allows the abovementioned major inconvenience to be avoided. To be more specific, the invention provides an electrochemical method for detecting a gaseous anhydride and measuring its concentration, in which the gas containing the gaseous anhydride to be detected does not necessarily come into contact with one of the metal electrodes that complete the electrochemical chain.

Another object of the invention is to provide an electrochemical method for detecting a gaseous anhydride and measuring its concentration in an oxygen-bearing gas, which method may be used over a wide range of concentrations from the low levels encountered in the environment to the very high levels found in the industrial stacks or in the emissions from other chemical or metallurgical processes.

More specifically, the invention provides a method for detecting sulfur anhydride or carbon anhydride and measuring its concentration in air or in an oxygen-bearing gas, which may be used for detecting and measuring concentrations ranging from less than 10 ppm to over 50,000 ppm.

A further object of this invention is to provide a method for detecting a gaseous anhydride and measuring its concentration in a gas in which the partial pressure of oxygen varies independently of the total pressure or gas flow rate.

Still another object of the invention is to provide a device for carrying out the invention, which device supplies a continuous, direct reading of the concentration of the anhydride in the gas of which the pollutant content is to be measured. More specifically, the invention provides a device that supplies a continuous signal, in millivolts, which is proportional to the logarithm of the activity of the anhydride to be detected and can be easily corrected to take into account the concentration or the partial pressure of the oxygen in the gas containing the anhydride to be detected.

An additional object of the invention is to provide a device for detecting sulfur anhydride or carbon anhydride and for measuring the concentration thereof in air or in an oxygen-containing gas, in which the anhydride to be detected, which may be present in a more or less oxidized form (mixture of sulfur dioxide, $SO_2$, and sulfuric anhydride, $SO_3$ or carbon monoxide, CO, and carbon dioxide, $CO_2$, for example), can be treated in such a way as to avoid reaching thermodynamic equilibrium, and thus allow a greater specificity of detection.

The method according to the invention for detecting a gaseous anhydride and measuring its concentration in an oxygen-bearing gas by measurement of a difference of potential, comprises the following steps:
- forming an electrolytic junction by contact between a first solid-electrolyte element containing oxyanions of the anhydride to be detected and a second solid-electrolyte element containing $O^{--}$ ions;
- bringing this electrolytic junction formed by the first and the second electrolyte elements into contact with the gas containing the gaseous anhydride to be detected, to form a triple junction;
- creating in this triple junction a difference of potential measurable by means of two reference electrodes in contact with the first and second electrolyte elements respectively, by fixing a constant potential in the vicinity of each of these reference electrodes, both of which are spatially removed from the triple junction;
- heating the triple junction to a temperature at which a logarithmic variation in the concentration of the anhydride to be detected produces a proportional, virtually linear variation in the difference of potential in this triple junction, this temperature being lower than the melting temperature of the first and second electrolyte elements; and measuring this difference of potential by means of a potentiometer connected to the reference electrodes so as to obtain a measurement of the concentration of the anhydride to be detected.

As may be noted, the method according to invention does not involve a triple contact between a solid-electrolyte element, a metal electrode and the gas containing the anhydride to be detected, which may be represented schematically as follows:

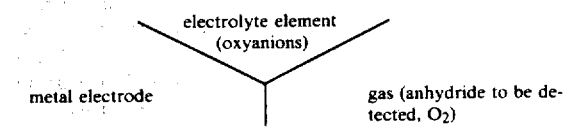

On the contrary, the method according to the invention involves a triple contact (or junction) between two solid-electrolyte elements and the gas containing the anhydride to be detected, which may be represented schematically as follows:

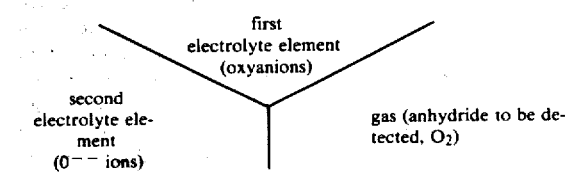

The gas containing the oxygen and the anhydride to be detected establishes an electrochemical equilibrium at the junction of the two solid-electrolyte elements. These two solid-electrolyte elements are each in contact with a reference electrode spatially removed from the previously defined triple junction. The reference electrodes are used to fix a potential in the vicinity of each of the electrodes by means of known techniques such as those described in the aforementioned Canadian and United States patents.

In practice, it has been demonstrated that measurement of the difference of potential between the two reference electrodes in contact with each of the two solid-electrolyte elements respectively, allows the potential at the junction to be measured and, consequently, the concentration of the anhydride to be detected. It has also been demonstrated that this measurement is easier to perform if the triple junction is heated in such a way that a logarithmic variation in the concentration of the anhydride to be detected produces a proportional, virtually linear variation in the measured difference of potential provided of course that, to keep this junction, the operating temperature must not exceed the melting temperature of either of the solid-electrolyte elements.

This may be explained theoretically as follows:

When the gas containing the oxygen and the anhydride to be detected, such as $SO_3$ for example, is in contact with the surface of the first solid-electrolyte element containing oxyanions of the anhydride to be detected, namely $SO_4^{--}$ ions, the concentration of the $O^{--}$ ions present in solid solution at the surface of this first solid-electrolyte element is equibrated. This equilibrium between the $O^{--}$ ions at the surface of the first electrolyte element and the sulfuric anhydride to be detected may be represented by the reaction:

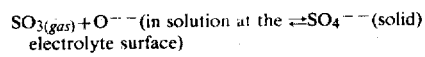

Theoretically, it may be supposed that the second solid-electrolyte element containing a fixed concentration of $O^{--}$ ions serves to measure the cncentration of $O^{--}$ ions in solid solution at the surface of the first electrolyte element with which it is in contact, provided that this $O^{--}$ ion concentration depends on the concentration of the anhydride to be detected in the gaseous phase. The second electrolyte element may therefore be considered as being acting as a specific-ion electrode for the $O^{-31}$ ions.

This assumed mechanism for the triple junction according to the invention may be compared to the assumption of R. Combes, J. Vedel and B. Tremillon in *Electrochim. Acta*, 20, 191 (1975) who describe the use of a zirconia electrode for measuring the $O^{--}$ ion activity in molten alkaline chloride mixtures. However, contrary to the assumption of the above authors, the concentration of $O^{--}$ ions in solid solution in the first electrolyte element is measured in accordance with the present invention only at the surface of this first electrolyte element, which is in contact with the gas containing the anhydride to be detected, and not in the bulk of the electrolyte element. For this reason, the desired triple junction must be optimized so as to promote the surface equilibrium of all species.

Known suitable methods already described in the literature, are used to fix constant reference potentials in the vicinity of each reference electrode.

To fix a constant equilibrium potential at the surface of the second, $O^{--}$ ion-conducting, solid-electrolyte element, air may be used or, alternatively, any couple formed by a metal and one of its oxides which, at a given temperature, can fix a suitable, constant partial pressure of oxygen.

Any known method may be used to fix a constant equilibrium potential at the surface of the first solid-electrolyte element containing oxyanions of the anhydride to be detected such as those described in Canadian Pat. Nos. 1.002.599 and 1.040.264 may be used. Thus, use can be made of a gas flow containing a known concentration of the anhydride to be detected for instance, or of an electrode of the Ag/Ag+type or of an electrode that produces the anhydride to be detected at a constant partial pressure by thermal decomposition at a given temperature or, finally, of an electrode that uses air and zirconia as a reference.

Based on the abovementioned assumption, the measurable difference of potential may be calculated theoretically. If $SO_3$ is to be detected, for instance, this difference of potential corresponds to the general formula:

$$E = E\text{ ref } ZrO_2(T^{III}) - E\text{ ref } SO_4^{--}(T^I) + \frac{RT^{II}}{2F}\ln[pSO_3^{II}]$$

where R is the constant of the perfect gases expressed in cal/mole/° C.; $T^I$, $T^{II}$ and $T^{III}$ are the temperatures expressed in ° K. near the first reference electrode, the triple junction and the second reference electrode, respectively; F is the constant of Faraday; E ref $ZrO_2$ and E ref $SO_4^{--}$ are the potentials created in the vicinity of each of the two reference electrodes and $[pSO_3^{II}]$ is the partial pressure of $SO_3$ in the vicinity of the electrolytic junction.

When operating at constant temperature, as proposed, the potentials E ref $ZrO_2$ and E ref $SO_4^{--}$ become fixed values and the value of the difference of potential E becomes $$E = \text{constant} + \frac{RT^{II}}{2F} \ln[pSO_3^{II}]$$

It may be seen immediately from this formula that the measured difference of potential effectively varies with the logarithm of the concentration of the anhydride to be detected near the electrolytic junction. This is in total agreement with the results of the measurements that were performed and are described hereinafter in the examples.

The method according to the invention for detecting a gaseous anhydride and measuring its concentration in an oxygen-bearing gas, can be carried out by using a detecting and measuring device which comprises:
- a first solid-electrolyte element containing oxyanions of the anhydride to be detected;
- a first reference electrode in contact with this first electrolyte element;
- means for fixing a constant potential near this first reference electrode;
- a second, $O^{--}$ ion-conducting, solid-electrolyte element spatially removed from the first reference electrode and in direct contact with the first electrolyte element so as to create a junction;
- a second reference electrode in contact with the second electrolyte element, this second reference electrode being spatially removed from the electrolytic junction;
- means for fixing a constant potential near this second reference electrode;
- means for bringing the electrolytic junction formed by the first and second electrolyte elements into contact with the gas containing the gaseous anhydride to be detected, so as to form a triple junction without the gas coming into contact with either of the reference electrodes;
- a potentiometer connected to the two reference electrodes to measure the difference of potential existing between these electrodes when the gas containing the anhydride to be detected is in contact with the junction formed by the first and second electrolyte elements, and
- means for heating the triple-electrolyte junction to a temperature at which a logarithmic variation in the concentration of the anhydride to be detected produces a proportional, virtually linear variation in the measured difference of potential, provided that this temperature does not exceed the melting temperatures of either the first or the second electrolyte elements.

In the device according to the invention, the first electrolyte element will preferably be composed of an alkaline or alkaline-earth salt containing oxyanions of the anhydride to be detected, and the second electrolyte element will be preferably composed of zirconia stabilized by doping with yttrium oxide, $Y_2O_3$, or calcium oxide, CaO.

In some specific cases, the concentration of gaseous anhydride to be detected can be influenced by the partial pressure of $O_2$ in the gas in contact with the electrolytic junction. Thus, in the specific case where the gas to be detected is $SO_2$, the concentration of $SO_3$ that will actually be measured will depend on the reaction temperature and on the concentration of $O_2$. This corresponds to the following chemical equilibrium;

$$SO_2 + \tfrac{1}{2}O_2 \rightleftharpoons SO_3$$

If $[SO_2]_i$ is used to describe the quantity of sulfurous anhydride contained in the gas to be analyzed in the device proposed in this invention, and $SO_{2e}$ and $SO_{3e}$ are used to describe the quantity of sulfurous and sulfuric anhydrides in equilibrium at the heating temperature, the resulting equation will be $$p[SO_2]_i = p[SO_2]_e + p[SO_3]_e$$

Using K to refer to the constant of equilibrium between the sulfurous and the sulfuric anhydrides, and expressing the value of $_p[SO_2]_e$ in the previous equation as a function of $_p[SO_3]_e$, the following equation is obtained:

$$p[SO_2]_i = p[SO_3]_e\left(1 + \frac{K}{p[O_2^{II}]^{\frac{1}{2}}}\right)$$

in which $_pO_2^{II}$ is the partial pressure of oxygen in the vicinity of the triple junction.

Replacing $_p[SO_3]_e$ by its value as a function of $_p[SO_2]_i$ in the theoretical value of the difference of potential given above, the following equation is obtained:

$$E = \text{constant} + \frac{RT}{2F} \ln p[SO_2] + \frac{RT}{4F} \ln p[O_2^{II}] - \frac{RT}{2F} \ln (K + p[O_2^{II}]^{\frac{1}{2}})$$

Therefore it may be observed, that if the concentration of $SO_2$ contained in a gas is to be measured with the device, according to the invention it will be preferable to operate at high partial pressures of $O_2$ and at a relatively low temperature, so that the difference between the last two terms in the previous equation become negligible and the measured potential difference be proportional to the logarithm of the $SO_2$ concentration contained in the gas irrespective of the concentration of $O_2$.

In the event that it be impossible to operate in the above indicated preferential conditions, another potentiometric detector may be used in conjunction with the device according to the invention to measure the concentration of $O_2$ in the gas containing the anhydride to be detected. The difference of potential measured by this other potentiometric detector then shall be subtracted, using any suitable electronic means, from the difference of potential measured by the device according to the invention to eliminate the influence and variation of the partial pressure of $O_2$ in the gas.

This other potentiometric detector can be an oxygen sensor, for example, such as that described in U.S. Pat. No. 3,400,054.

The invention will be better understood from the following non-restrictive description of several preferred embodiments and practical examples, with reference to the attached drawings in which:

FIG. 1 represents a diagramatic view of a detecting and measuring device according to the invention, comprising two compartments, one of which contains a reference atmosphere for the first electrolyte element, the other containing an atmosphere for measuring the concentration of the anhydride to be detected, this measuring atmosphere serving also as a reference atmosphere for the second electrolyte element;

FIG. 2 represents a diagrammatic view of a detecting and measuring device according to the invention comprising three separate compartments, one of which contains a reference atmosphere for the first electrolyte element, the other containing an atmosphere for measuring the cncentration of the anhydride to be detected while the third compartment contains a reference atmosphere for the second electrolyte element;

Figure 1:
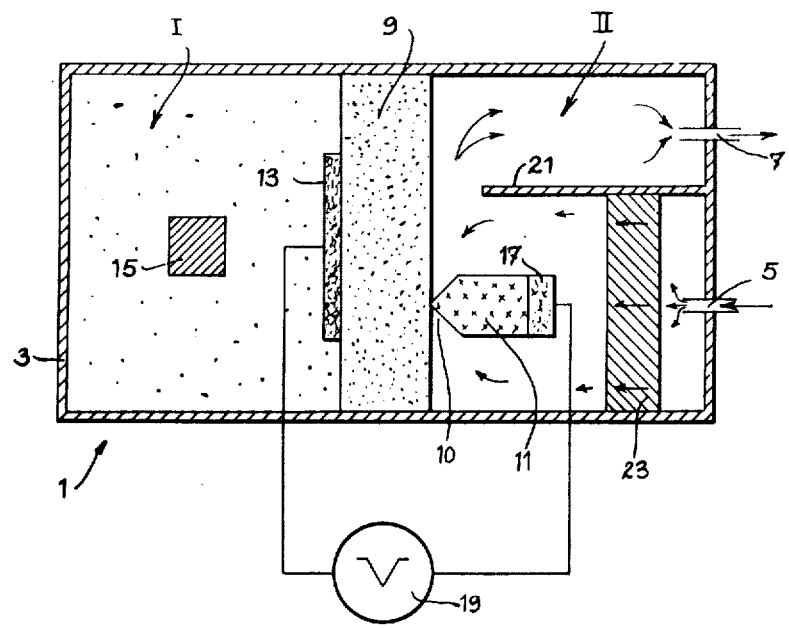
Figure 5:
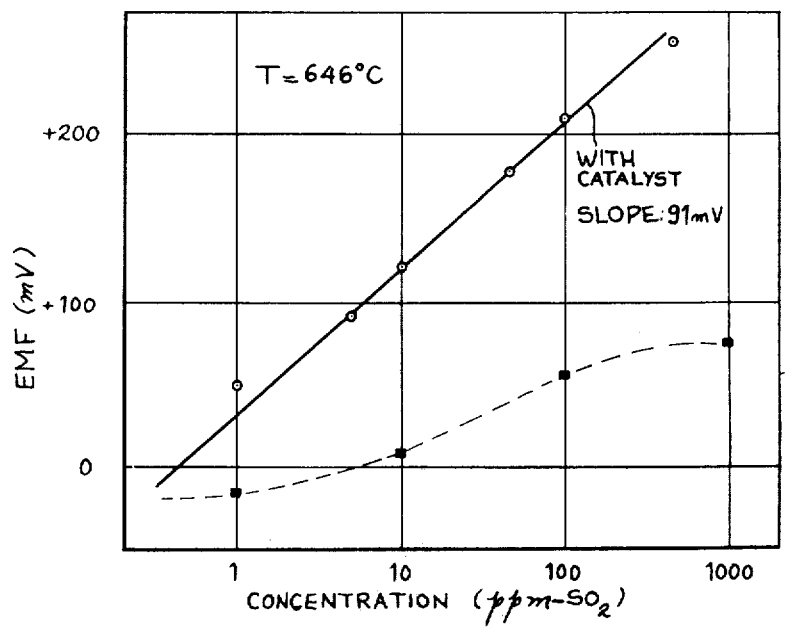
Figure 6:
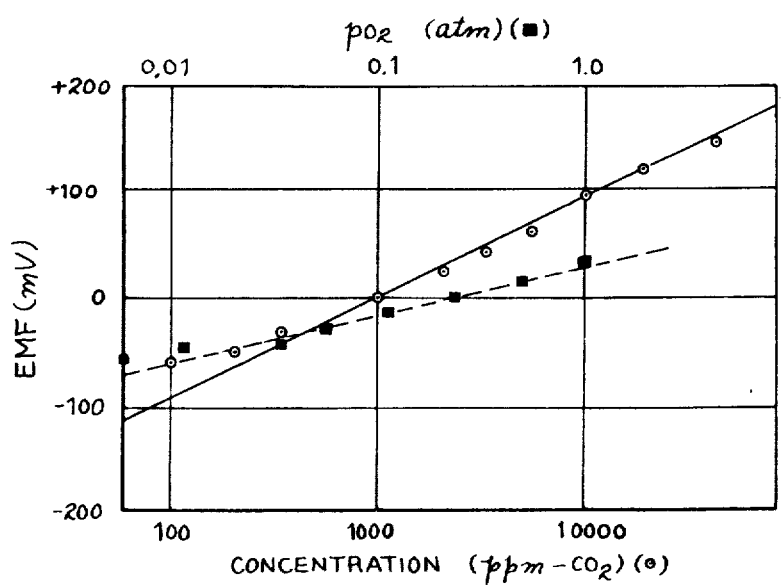
Figure 7:
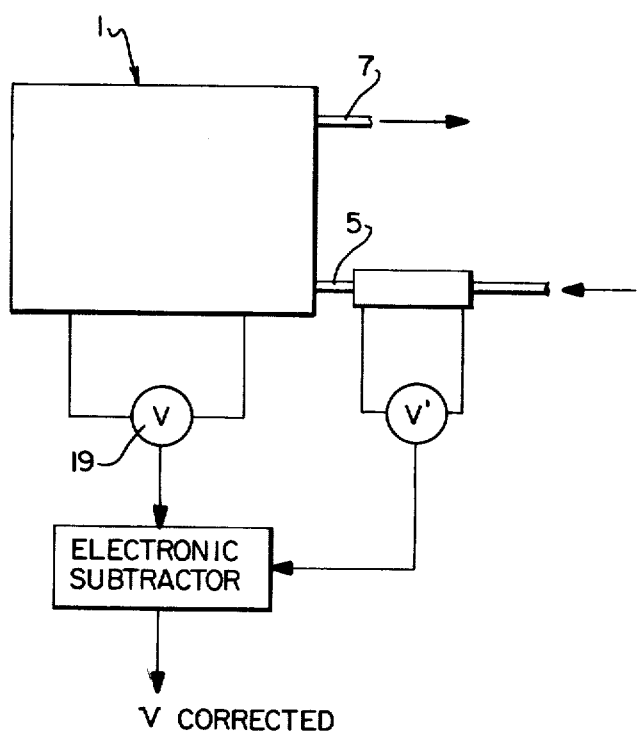

FIG. 5 represents curves of the differences of potential measured experimentally with a device as illustrated in FIG. 1, as a function of various $SO_2$ concentrations to be detected; and FIG. 6 represents curves of the differences of potential measured experimentally as a function of various $CO_2$ concentrations at a constant $O_2$ partial pressure, and of variable $O_2$ partial pressure at a constant $CO_2$ concentration, and FIG. 7 represents a diagrammatic view of a detecting and measuring device according to one embodiment of the invention comprising two potentiometric detectors and a means for subtracting the difference of potential measured by the second potentiometric device (measuring the oxygen concentration of the gas containing the anhydride to be detected) from the first potentiometric device (measuring gaseous anhydride concentration). The substracting means may, for example, comprise an electronic subtractor.

FIG. 1 diagrammatically shows a detecting and measuring device 1 comprising two compartments I and II, each of which has its own atmosphere.

The device 1 comprises a first solid-electrolyte element 9 which contains oxyanions of the gaseous anhydride to be detected. The first solid-electrolyte element 9 consists preferably of an alkaline or alkaline-earth salt and is in the general shape of a pellet obtained by pressing and sintering the corresponding powder. The pellet is tightly fitted inside a tube 3. The ends of this tube 3 are sealed to form the compartments I and II inside the tube, with separate atmospheres. The tube 3 may be made of alumina, silica, or any other suitable refractory material.

The compartment I which is defined by a part of tube 3 and one of the surfaces or the first electrolyte element 9, is used to fix a reference potential for the first electrolyte element 9. For this purpose, compartment I contains a powder 15 consisting of a mixture of an oxyanion and its oxide which, upon decomposition at a given temperature, produces a metal oxide and a certain quantity of an anhydride identical to the anhydride to be detected at a constant partial pressure according to the following equilibrium

M[oxyanion]⇌MO+[anhydride to be detected]

The surface of the first electrolyte element 9 in contact with the atmosphere created by the powder 15 in compartment I, is also in contact with a reference electrode 13 made of an electronically conducting, porous material such as a platinum or gold wire, mesh or felt. A metal wire runs from this reference elecrode 13 to one of the terminals of a potentiometer 19 located outside the tube 3, through a tight passage provided for this purpose into the tube.

It should be noted that the metal electrode 13 and the powder 15 used to produce a constant partial pressure of the anhydride to be detected in compartment I, may be replaced by a conventional reference electrode used in combination with a gas containing a known concentration of the anhydride to be detected, or by an electrode of the $Ag/Ag^+$ type in direct contact with the first electrolyte element, or by an electrode made of stabilized zirconia and used in the presence of air so as to create a constant electromotive force and to fix a reference potential at the surface of the first electrolyte element 9. The alternative methods that can be used to fix this reference potential in compartment I are known and have already been described in detail in the above mentined Canadian Patents 1.002.599 and 1.040.264.

The gastight compartment II which is defined by the other part of the tube 3 and the other surface of the first electrolyte element 9, contains a second electrolyte element 11 comprising a constant concentration of $O^{--}$ ions. This second electrolyte element 11, which may consist of stabilized zirconia, is in direct contact with the surface of the first electrolyte element 9 with which it forms an electrolytic junction 10. The end of the second electrolyte element 11 in contact with the first electrolyte element 9 is preferably cone-shaped so as to optimize equilibrium with the gas phase at the electrolytic junction. The other end or side of this second electrolyte element is in contact with a second reference electrode 17 identical in structure and composition to the reference electrode 13. A metal wire runs from this second reference electrode 17 to the other terminal of the potentiometer 19, through a gastight passage provided for this purpose in the wall of the tube 3.

The oxygenated gas containing the gaseous anhydride whose concentration is to be determined, enters compartment II via a ceramic, glass or metal inlet 5 tightly sealed in the end of tube 3. This inlet 5 is preferably in an axial position with respect to the tube to allow better contact between the gas and the first and second electrolyte elements 9 and 11. The gas, shown in FIG. 1 by small arrows, passes through a pellet of porous catalytic material 23, the purpose of which is to promote, if necessary, a thermodynamic equilibrium between the oxygen and the various oxidation forms of the anhydride to be detected. After passing through the catalytic material, the gas whose anhydride concentration is to be measured, is directed to the electrolytic junction 10 by a wall 21 axially positioned inside compartment II, to form a triple junction with the first and second solid-electrolyte elements 9 and 10. The gas, which contains the anhydride to be detected and a certain amount of oxygen, creates potentials at the triple junction 10 and at the surface of the second electrode 17.

The sum of the various electromotive forces thus created at each of the reference electrodes 13 and 17 and at the junction 10 is then measured by the potentiometer 19.

Finally, the gas that enters compartment II via inlet 5 is exhausted via an outlet 7 tightly sealed in the wall of the tube 3, after it has passed the end of the internal wall 21.

To improve the operating efficiency of the electrolyte elements 9 and 11, the tube 3 is placed in an electric oven (not shown) and heated to a suitable temperature selected in such a way that a logarithmic variation in the activity of the anhydride to be detected results in a variation proportional to and virtually linear with the measured difference of potenial (see FIGS. 5 and 6).

Figure 2:
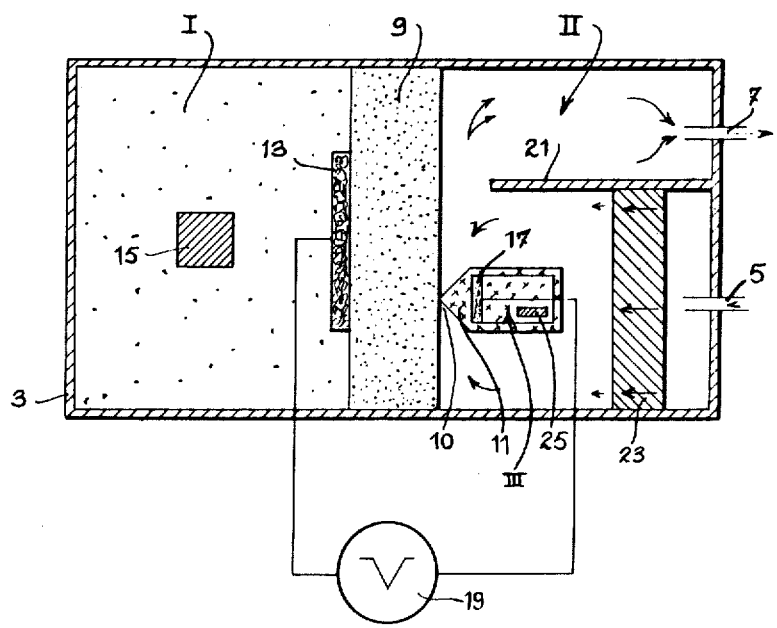

FIG. 2 diagrammatically shows a variant of the above described detecting and measuring device. This variant comprises three compartments I, II and III each of which has a separate atmosphere.

For the sake of simplicity, the various structural elements shown in FIG. 2 bear the same number as their counterparts in FIG. 1, the structure being almost identical.

The main difference between the device illustrated in FIG. 1 and the variant shown in FIG. 2 lies in the structure of the second electrolyte element 11.

As can be seen, the second electrolyte element 11 shown in FIG. 2 comprises an internal cavity, which forms a third compartment III. The reference electrode 17 is located in the compartment III and is in contact with the internal wall of the second electrolyte element 11 which, as aforesaid, may consist of a cone of stabilized zirconia.

As also aforesaid, an electric wire connects the reference electrode 17 to one of the terminals of a potentiometer 19 via a first gastight, electrically insulated passage provided for this purpose in the wall of the second electrolyte element 11 and a second gastight, electrically insulated passage provided in the wall of the tube 3.

In addition to the reference electrode 17, the gastight compartment III formed within the second electrolyte element 11, comprises a powder 25 composed of a metal and one of its oxides, such as a mixture of nickel and nickel oxide which, at a given temperature, fixes a constant $O_2$ partial pressure. The atmosphere created by this powder 25 in compartment III serves to establish a constant reference potential at the internal surface of the second electrolyte element 11 which is in contact with the reference electrode 17. This original arrangement is extremely advantageous in that it avoids contact between the gas circulating at the electrolytic junction and whose anhydride concentration is to be measured, and the reference electrodes. This eliminates the risk of these electrodes being exposed to aging phenomena, such risk being usually encountered in known similar devices, especially when the gas to be measured is extremely contaminated.

As previously, the tube 3 of the device illustrated in FIG. 2 is placed in an electric oven (not shown) and heated to a temperature at which the operating efficiency of the electrolyte elements 9 and 10 in increased namely a temperature high enought to obtain satisfactory conductivity of each of the electrolyte elements and rapid reaction rates between the solid and gas phases.

This heating temperature, which is normally ranging between 400° C. and the melting temperature of one or the other of the solid-electrolyte elements, permits to obtain substantially linear variation in the measured difference of potential as a function of the logarithm of the activity of the anhydride to be detected. The existence of this linear relationship between the logarithm of the activity and the measured potential difference permits an immediate, correct interpretation of the results obtained at a given temperature.

As mentioned previously, the heating temperature must always be lower than the melting temperature of one or other of the solid-electrolyte elements used in the tube in order to preserve their solid-state characteristics.

The following examples will provide a better illustration of the advantages of the devices shown in FIGS. 1 and 2.

EXAMPLE 1

A series of analyses was carried out using the device shown in FIG. 1 to determine various contents of sulfur dioxide ($SO_2$) in air. Different amounts of $SO_2$ varying from 3 to 10,000 ppm were drawn into compartment II of the device 1 at a flow rate of 50 cc/min and a temperature of 780° C. For this experiment, the first electrolyte element 9 consisted of a pellet of potassium sulfate, $K_2SO_4$, and the second electrolyte element 11 of a cone of zirconia, $ZrO_2$, stabilized with yttrium oxide, $Y_2O_3$. The metal used for the electrodes 13 and 17 was platinum and the powder 15 used to fix the potential of the reference electrode 13 in compartment I was a mixture of magnesium sulfate and magnesium oxide.

Figure 3:
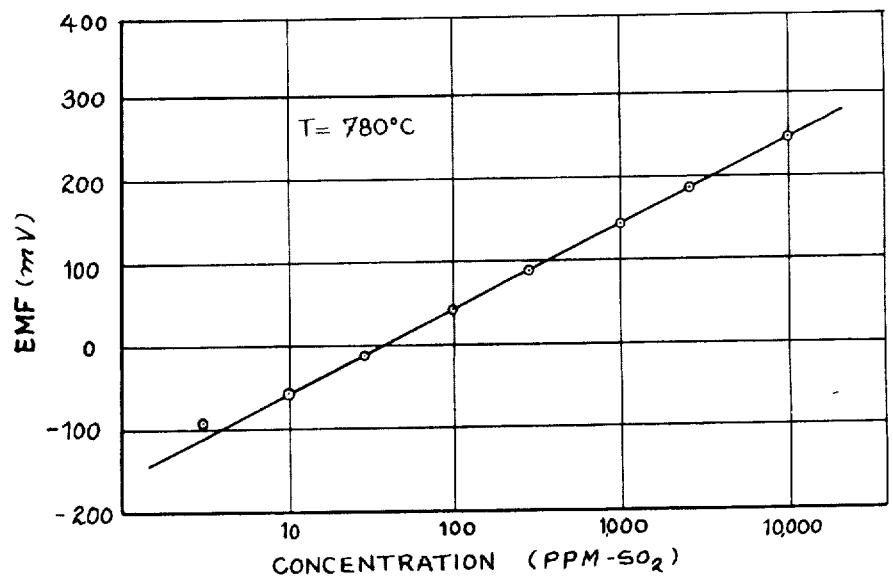
FIG. 3 represents a curve of the differences of potential measured experimentally with a device such as that illustrated in FIG. 1, as a function of various partial pressures of $SO_2$ in air.

The results obtained, as plotted in FIG. 3, show that the measured difference of potential varies linearly with the logarithm of the $SO_2$ concentration in air.

It should be noted that these analyses were repeated at flow rates varying between 1 and 500 cc/min and temperatures ranging between 400° C. and the melting point of the solid-electrolyte element with the lowest melting point, with results similar to those given in FIG. 3

The value of the potential difference calculated theoretically for this type of two-compartment device corresponds to the formula:

$$E = \text{const.} + \frac{RT^{II}}{2F} \ln (pSO_3^{II}) + \frac{RT^{II}}{4F} \ln pO_2^{II}$$

where R is the constant of the perfect gases in cal/mole/°C.; $T^{II}$ is the temperature in degrees Kelvin in compartment II; F is the constant of Faraday; $pSO_3^{II}$ is the partial pressure of $SO_3$ near the electrolytic junction; and $pO_2^{II}$ is the partial pressure of $O_2$ near the electrolytic junction.

If the content of $SO_3$ in compartment II is expressed as a function of the content of $SO_2$ admitted, the previous formula becomes:

$$E = \text{const.} + \frac{RT}{2F} \ln pSO_{2i} + \frac{RT}{2F} \ln pO_2 - \frac{RT}{2F} \ln (K + pO_2^{\frac{1}{2}})$$

where the constant is a fixed value which depends only on the choice of reference electrodes; K is the equilibrium constant of the reaction $SO_2 + \frac{1}{2}O_2 \rightleftarrows SO_3$; $pSO_{2i}$ is the partial pressure of $SO_2$ admitted; and $pO_2$ is the partial pressure of $O_2$ in the gas admitted.

When the partial pressure of $O_2$ is almost identical to the partial pressure of $O_2$ in air, the last two terms in the previous formula become constants, which means that the theoretical slope derived from the plot of the potential E as a function of the $SO_2$ concentration for a temperature of 780° C. is equal to:

$2.3 \times (RT/2F) = 104 \text{mV/decade of concentration}$

This theoretical slope shows good correspondence with the slope obtained experimentally in FIG. 3.

EXAMPLE 2

In order to verify the operation of the device illustrated in FIG. 2, three series of analyses were performed using gas mixtures containing a constant $SO_2$ concentration but variable $O_2$ concentrations at temperatures of 595, 705 and 780° C.

These analyses were performed using potassium sulfate as first electrolyte element, yttrium-stabilized zirconia as second electrolyte element and platinum as electrodes 13 and 17. The powder 15 was a mixture of $MgSO_4/MgO$ and the powder 25 a mixture of $Pd/PdO$. The analyses were performed using a fixed $SO_2$ content of 100 ppm, a flow rate of 100 cc/min and an $O_2$ partial pressure varying from $3.10^{-4}$ to 1 atm.

Figure 4:
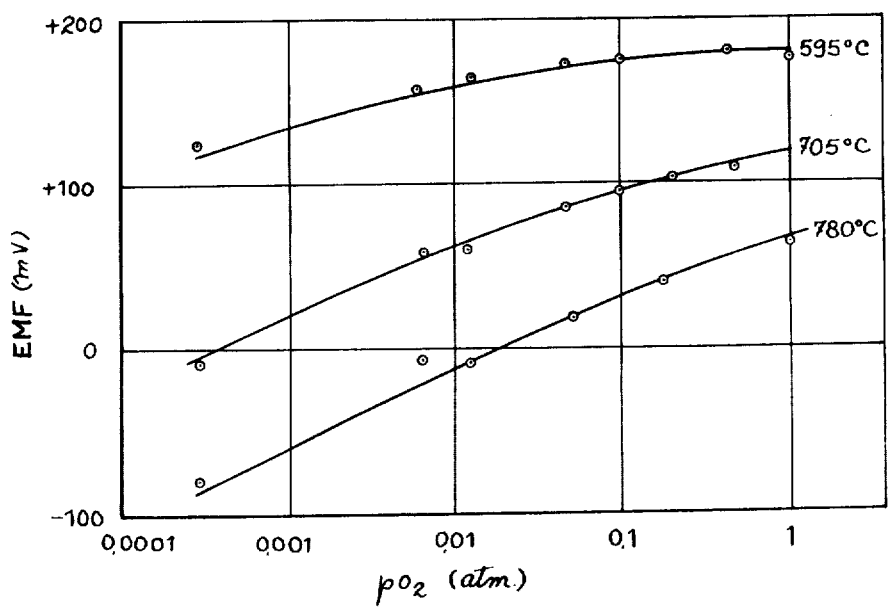
FIG. 4 represents curves of the differences of potential measured experimentally at a constant $SO_2$ concentration with a device such as that illustrated in FIG. 2, as a function of various $O_2$ partial pressures at three different temperatures, the points representing the experimental results while solid line representing the theoretically derived performance.

The results obtained experimentally are represented by the points in FIG. 4. These points are superposed on the curve of the value of the potential difference calculated theoretically for such a three-compartment device, which corresponds to the formula:

$$E = \text{const.} + \frac{RT^{II}}{2F} \ln (pSO_3^{II})$$

Expressed in terms of the content of $SO_2$ admitted into the device, this formula becomes:

$$E = \text{const.} + \frac{RT}{2F} \ln pSO_{2i} + \frac{RT}{4F} \ln pO_2 - \frac{RT}{2F} \ln (K + pO_2^{\frac{1}{2}})$$

According to this theoretical formula, the value of the potential difference as a function of the $O_2$ content should vary almost linearly with a slope equal to $RT/4F$ when the $O_2$ content is low, and should show a tendency to become independent of the $O_2$ content when the $O_2$ partial pressure reaches a high level, particularly at low temperature.

It may be seen from FIG. 4 that the experimental results entirely agree with this theoretical behavior derived from the formula above.

Consequently, in order to obtain measurements of the $SO_2$ concentration that are independent of the $O_2$ partial pressure in the sample analyzed, the following procedure should be adopted:

(1) In the case of a gas having an $O_2$ content of over 1%.

It is preferable to perform the measurements at a temperature lower than 550° C. This means that no corrections will be needed, since the $O_2$ partial pressure will have a negligible influence on the measured value of the potential difference.

(2) In the case of a gas having an $O_2$ content of less than 1%:

It is preferable to perform the measurements at a temperature higher than or equal to 800° C. In this case, the measured potential difference will show a linear variation as a function of the $O_2$ partial pressure with a slope equal to $RT/4F$. This linear variation can be easily corrected by using another potentiometric detector in conjunction with the device 1, to measure only the $O_2$ concentration in the gas to be analyzed, together with suitable electronic means for subtracting the potential difference measured by this other potentiometric detector from the potential difference measured by the device 1. Any potentiometric sensor usable for detecting oxygen, such as a zirconia sensor, operating at the same temperature as the device may be used for measuring this $O_2$ partial pressure.

EXAMPLE 3

Two series of analyses were performed using a two-compartment device as shown in FIG. 1.

The first series of experimental results obtained are illustrated by the solid-line curves in FIG. 5. These results show the value of the measured difference of potential as a function of different $SO_2$ concentrations in air when a catalyst 23 is used downstream the inlet 5 in the device 1. The basic function of this catalyst 23 is to allow the gaseous phase to complete its predicted chemical equilibrium between $SO_2$, $SO_3$ and $O_2$ before the mixture reaches the junction 10 between the two solid-electrolyte elements 9 and 11.

In this case, difference of potential between the two reference electrodes is expressed theoretically as:

$$E = \text{const.} + \frac{RT}{2F} \ln pSO_{2i} + \frac{RT}{2F} \ln pO_2 - \frac{RT}{2F} \ln (K + pO_2^{\frac{1}{2}})$$

As in the case of example 1, the last two terms of this formula become constants, with the result that $$E = \text{const.} + \frac{RT}{2F} \ln pSO_{2i}$$

This theoretical behavior is in full agreement with the experimental results plotted in FIG. 5.

The second curve, shown in dashed line in FIG. 5, follows the plots obtained under the same conditions when no catalyst is used. In this case, the gas-phase equilibrium is not reached, with the result that the measured potential difference does not vary linearly with the logarithm of the concentration of the $SO_2$ admitted, as may be noticed from the experimental results obtained.

In both cases, a pellet of $K_2SO_4$ was used as first electrolyte element and stabilized zirconia as second electrolyte element; the flow rate was 150 cc/min and the operating temperature was 646° C. The metal of the electrodes and the powders 15 and 25 were identical to those employed in the preceeding example.

It should be noted that, in some cases, it may be advantageous not to catalyze the gaseous phase to be analyzed until it has come into contact with the two electrolyte elements. This might be advantageous, for example, for the specific detection of $SO_3$ in a gas sample without measuring the total sulfur dioxide and trioxide content drawn into the device.

EXAMPLE 4

A series of analyses was performed with the device illustrated in FIG. 1 using gas samples containing a variable concentration of $CO_2$ in air in one case, and a constant concentration of $CO_2$ in a mixture containing a variable $O_2$ concentration, in a second case.

In both cases, the analyses were performed using potassium carbonate as first electrolyte element, and a lime-doped zirconia cone as second electrolyte element; the gas flow rate was 100 cc/min and the temperature 760° C. Gold was used as electrode 13, platinum as electrode 17. The powder 15 was a mixture of $CaCO_3$ and CaO.

Contrary to the previous analyses carried out with $SO_2$, it was not necessary here to use a catalyst 23 since at the temperature at which the analyses were performed, $CO_2$ is the thermodynamically favored form of carbon oxides. It should be noted, however, that, in order to analyze a gas containing CO, total combustion of the CO into $CO_2$ should be ensured before the gas reaches the junction of the detecting device.

When the anhydride to be analyzed is carbon dioxide, the value of the theoretically calculated difference of potential, in the case of the two-compartment device, is expressed as:

$$E = \text{const.} + \frac{RT}{2F} \ln pCO_2 + \frac{RT}{4F} \ln pO_2$$

The first series of measurements performed by varying the $O_2$ partial pressure at a constant $CO_2$ partial pressure shows very clearly that the difference of potential varies linearly according to a slope equal to RT/4F (see the dashed curve in FIG. 6). Similarly, the experimental results obtained by varying the $CO_2$ content from 100 to 40,000 ppm at a constant $O_2$ concentration show that the measured difference of potential varies linearly according to a slope of RT/2F (see the solid-line curve in FIG. 6).

It follows, therefore, that to measure the $CO_2$ content in a gas containing variable $O_2$ concentrations, an oxygen sensor must be used. By subtracting the potential difference measured by this oxygen sensor from that measured by the two-compartment device 1 illustrated in FIG. 1, the value of the $CO_2$ concentration can be determined.

If a three-compartment device such as that illustrated in FIG. 2 is used, the theoretically claculated value of the potential difference would be expressed as:

$$E = \text{const.} + \frac{RT}{2F} \ln pCO_2$$

Since this value is independent of the $O_2$ partial pressure in the gas to be analyzed, no correction is necessary which, from a practical point of view, is extremely advantageous.

Obviously, the embodiments and examples described above are preferential forms of the invention, the scope of which is limited only by the following claims.

What is claimed is:

1. A device for detecting a gaseous anhydride and measuring its concentration in an oxygen-bearing gas, said device comprising:

a first solid-electrolyte element containing oxyanions of the anhydride to be detected;

a first reference electrode in contact with said first electrolyte element;

means for fixing a constant potential near this first reference electrode;

a second, O$^{--}$ ion-conducting, solid-electrolyte element, said solid-electrolyte element being spaced from said first reference electrode and in direct contact with said first electrolyte element so as to create an electrolytic junction;

a second reference electrode in contact with said second electrolyte element, said second reference electrode being spaced from said electrolytic junction;

means for fixing a constant potential near this second reference electrode;

means for bringing the gas containing the gaseous anhydride to be detected into contact with the electrolytic junction formed by the first and second electrolyte elements so as to form a triple junction, means for preventing contact of said gas and said first reference electrode;

a potentiometer connected to said reference electrodes to measure the difference of potential existing between said reference electrodes when the gas containing the gaseous anhydride to be detected is in contact with the electrolytic junction formed by the first and second electrolyte elments, and means for heating said triple junction to a temperature at which a logarithmic variation in the concentration of the anhydride to be detected produces a proportional, virtually linear variation in the measured difference of potential, provided that said temperature is lower than the melting temperatures of said first and second electrolyte elements.

2. A device as claimed in claim 1, characterized in that the first electrolyte element consists of an alkaline or alkaline-earth salt containing oxyanions of the anhydride to be detected.

3. A device as claimed in claim 2, characterized in that the anhydride to be detected is sulfur anhydride and the oxyanions contained in said first electrolyte element are sulfate ions.

4. A device as claimed in claim 2, characterized in that the anhydride to be detected is carbon anhydride and the oxyanions contained in said first electrolyte element are carbonate ions.

5. A device as claimed in claims 2, 3 or 4 characterized in that the first electrode is of metal and the means for fixing a constant potential near the first electrode consists of a salt of the same type of metal as the first electrode, said metal salt having been dissolved in said first electrolyte element in such a way that it is in contact with the metal of the first electrode.

6. A device as claimed in claims 2, 3 or 4, characterized in that the means for fixing a potential near the first reference electrode consists of a salt of the oxyanion of the anhydride to be detected which, upon thermal decomposition at a given temperature, produces a metal oxide and the anhydride to be detected at a constant partial pressure.

7. A device as claimed in claims 2, 3 or 4, characterized in that the means for fixing a constant potential near the first reference electrode consists of a flow of gas containing a given concentration of the anhydride to be detected said gas circulating near the first reference electrode.

8. A device as claimed in claim 1, characterized in that the second solid electrolyte element is an O$^{--}$ ion-conducting oxide.

9. A device as claimed in claim 8, characterized in that the O$^{--}$ ion-conducting oxide is zirconia stabilized with $Y_2O_3$.

10. A device as claimed in claim 8, characterized in that the O$^{--}$ ion-conducting oxide is zirconia stabilized with CaO.

11. A device as claimed in claims 8, 9 or 10, characterized in that the means for fixing a constant potential near the second reference electrode consists of a mixture of a metal and one of its oxides which, at a given temperature, can fix a constant $O_2$ partial pressure near this second reference electrode, said second reference electrode being out of contact with the gas containing the gaseous anhydride to be detected.

12. A device as claimed in claims 8, 9 or 10, characterized in that the means for fixing a constant potential near the second reference electrode consists of a flow of gas containing a constant concentration of $O_2$, said flow of gas circulating near the second reference electrode.

13. A device as claimed in claim 1, characterized in that it is housed in an enclosure defining:
   a first reference compartment containing the first reference electrode and the means for fixing a constant potential near this first reference electrode;
   a second reference compartment containing the second reference electrode and the means for fixing a constant potential near this second reference electrode, and
   a central compartment containing the electrolytic junction formed by the first and second electrolyte elements, a supply line for the gas containing the gaseous anhydride to be detected, and an outlet for said gas.

14. A device as claimed in claim 13, characterized in that both reference compartments are independant from each other and both sealed off from the atmosphere in the central compartment.

15. A device as claimed in claim 13, characterized in that the central compartment and the second reference compartment together form a single compartment which is supplied with the gas containing oxygen and the anhydride to be detected.

16. A device as claimed in claim 1, characterized in that the potentiometer is a voltmeter.

17. A device as claimed in claim 1, characterized in that it also comprises another potentiometric detector for measuring the oxygen concentration of the gas containing the anhydride to be detected, and means for subtracting the difference of potential measured by this other potentiometric detector from the difference of potential measured by the device for detecting and measuring the gaseous anhydride concentration, in order to eliminate the influence of the variation in the $O_2$ partial pressure in the gas.

18. A device as claimed in claim 17, characterized in that the gaseous anhydride to be detected is sulfur anhydride, the oxyanions contained in the first electrolyte element are sulfate ions and the gas containing the sulfur anhydride to be detected is brought into contact with the electrolytic junction formed by the first and second electrolyte elements.

19. A device as claimed in claim 17, characterized in that the gaseous anhydride to be detected is carbon anhydride, the oxyanions contained in the first electrolyte element are carbonate ions and the gas containing the carbon anhydride is brought into contact with the electrolytic junction formed by the first and second electrolyte element.

20. A device as claimed in claims 17 or 18, characterized in that the second solid-electrolyte element is composed of zirconia stabilized with $Y_2O_3$.

21. A device as claimed in claims 17, 18 or 19, characterized in that the second solid-electrolyte consists of zirconia stabilized with CaO.

22. A method for detecting a gaseous anhydride and measuring its concentration in an oxygenbearing gas by measurement of a difference of potential, characterized in that it comprises the following steps:

forming an electrolytic junction by contact between a first solid-electrolyte element containing oxyanions of the anhydride to be detected and a second, solid-electrolyte element containing $O^{--}$ ions;
bringing the gas containing the gaseous anhydride to be detected into contact with said electrolytic junction formed by the first and second electrolyte elements to form a triple junction;
creating in this triple junction a difference of potential measurable by means of two reference electrodes in contact with said first and second electrolyte elements respectively, by fixing a constant potential in the vicinity of each of said reference electrodes, said reference electrodes being both spaced from the triple junction, the reference electrode in contact with said first electrolyte element being out of contact with the anhydride containing gas;
heating said triple junction to a temperature at which a logarithmic variation in the concentration of the anhydride to be detected produces a proportional, virtually linear variation in the difference of potential in said triple junction, said temperature being lower than the melting temperatures of said first and second electrolyte elements, and
measuring said difference of potential with a potentiometer connected to said reference electrodes so as to obtain a measurement of the concentration of the anhydride to be detected.

23. A method as claimed in claim 22 for detecting sulfur anhydride and measuring its concentration in an oxygen-bearing gas, characterized in that said first and second electrolyte elements forming the junction consist respectively of an alkaline or alkaline-earth salt containing sulfate ions, and stabilized zirconia.

24. A method as claimed in claim 22 for detecting carbon anhydrides and measuring its concentration in an oxygen-bearing gas, characterized in that said first and second electrolyte elements forming the electrolyte junction consist respectively of an alkaline or alkaline-earth salt containing carbonate ions, and stabilized zirconia.

25. A method as claimed in claims 23 or 24, characterized in that the first reference electrode is made of metal and a constant potential is fixed near this first reference electrode by bringing the metal of said first reference electrode into contact with the first electrolyte element after having dissolved in the latter a metal salt of the same metal as that of the first reference electrode.

26. A method as claimed in claims 23 or 24, characterized in that a constant potential is fixed near the first reference electrode by placing near this first reference electrode a salt of the oxyanion to be detected which, upon thermal decomposition at a given temperature, produces a metal oxide and the anhydride to be detected at a constant partial pressure.

27. A method as claimed in claims 23 or 24, characterized in that a constant potential is fixed near the first reference electrode by circulating a gas flow containing a given concentration of the anhydride to be detected near said first reference electrode.

28. A method as claimed in claims 23 or 24, characterized in that a constant potential is fixed near the second reference electrode by placing near said second reference electrode a mixture of a metal and one of its oxides which, at a given temperature, fixes a constant $O_2$ partial pressure near this second reference electrode.

29. A method as claimed in claims 23 or 24, characterized in that a constant potential is fixed near the second reference electrode by circulating a gas flow containing a constant concentration of $O_2$ near said second reference electrode.

30. A method as claimed in claims 22, 23 or 24, characterized in that the gas containing the anhydride to be detected is brought into contact with both the electrolytic junction and the second electrolyte element near the second reference electrode.

31. A method as claimed in claims 22, 23 or 24, characterized in that the gas containing the gaseous anhydride to be detected is circulated through another potentiometric detector to measure the $O_2$ concentration in this gas, and the difference of potential measured by this other potentiometric detector is subtracted from that measured by the potentiometer used for measuring the concentration of gaseous anhydride in order to eliminate the influence of the variation in the partial pressure of $O_2$ in the gas.

* * * * *